United States Patent [19]
Simonnet

[11] Patent Number: 5,958,433
[45] Date of Patent: Sep. 28, 1999

[54] STABLE DISPERSION OF A WATER-IMMISCIBLE PHASE, IN AN AQUEOUS PHASE BY MEANS OF VESICLES BASED ON SILICONE SURFACTANT

[75] Inventor: Jean-Thierry Simonnet, Paris, France

[73] Assignee: L'Oreal, Paris, France

[21] Appl. No.: 08/771,840

[22] Filed: Dec. 23, 1996

[30] Foreign Application Priority Data

Dec. 21, 1995 [FR] France ................................. 95 15292

[51] Int. Cl.$^6$ ............................. A61K 7/00; A61K 9/113; A61K 9/127
[52] U.S. Cl. ......................... 424/401; 424/400; 424/450; 424/455; 514/938
[58] Field of Search ................... 424/400, 401, 424/450, 445; 514/938

[56] References Cited

U.S. PATENT DOCUMENTS 5,364,633  11/1994  Hill .......................................... 424/450

FOREIGN PATENT DOCUMENTS

| | | |
|---|---|---|
| 0 043 327 | 1/1982 | European Pat. Off. . |
| 0 226 337 | 6/1987 | European Pat. Off. . |
| 0 330 369 | 8/1989 | European Pat. Off. . |
| 0 407 089 | 1/1991 | European Pat. Off. . |
| 0 444 983 | 9/1991 | European Pat. Off. . |
| 0 514 934 | 11/1992 | European Pat. Off. . |
| 0 526 289 | 2/1993 | European Pat. Off. . |
| 0 529 847 | 3/1993 | European Pat. Off. . |
| 0 559 013 | 9/1993 | European Pat. Off. . |
| 0 579 455 | 1/1994 | European Pat. Off. . |
| 0615741 | 9/1994 | European Pat. Off. . |
| 0 631 774 | 1/1995 | European Pat. Off. . |
| 0 638 308 | 2/1995 | European Pat. Off. . |
| 0638308 | 2/1995 | European Pat. Off. . |
| 2 315 991 | 1/1977 | France . |
| 2 597 345 | 10/1987 | France . |
| 2 597 367 | 10/1987 | France . |
| 2 683 453 | 5/1993 | France . |
| 2 693 466 | 1/1994 | France . |

OTHER PUBLICATIONS

Tenside, Surfactant, Detergents, vol. 29, No. 2, Mar. 1992, Münich, pp. 78–83, XP002012394, B. Grüning et al.

*Primary Examiner*—Shelley A. Dodson
*Attorney, Agent, or Firm*—Oblon, Spivak, McClelland, Maier & Neustadt, P.C.

[57] ABSTRACT

A dispersion of a water-immiscible phase, in an external aqueous phase by means of lipid vesicles comprising at least one silicone surfactant, for the treatment of the skin, the mucous membranes, the nails, the scalp and the hair and in particular, greasy skin.

26 Claims, No Drawings

STABLE DISPERSION OF A WATER-IMMISCIBLE PHASE, IN AN AQUEOUS PHASE BY MEANS OF VESICLES BASED ON SILICONE SURFACTANT

BACKGROUND OF THE INVENTION

1. Field of the Invention

The present invention relates to a dispersion of a water-immiscible phase in an aqueous external or continuous phase by means of lipid vesicles comprising a silicone surfactant, and to its use for the treatment of the skin, the mucous membranes, the nails, the scalp and/or the hair.

"Lipid vesicles" is understood to mean particles formed of a lamellar phase consisting of one or more concentric sheets, these sheets comprising one or more bimolecular layers of amphiphilic lipids encapsulating an aqueous phase. The encapsulated aqueous phase may contain water-soluble active substances and the bimolecular layers of amphiphilic lipids may contain lipophilic active substances.

2. Description of Background

It is known in the cosmetic and dermatological fields to apply to the skin compositions in the form of aqueous dispersions containing a water-immiscible phase and lipid vesicles which bring about the dispersion of the water-immiscible phase in the aqueous phase.

Thus, documents FR-A-2,490,504 and FR-A-2,485,921 describe the stabilization of a dispersion of droplets of a water-immiscible liquid and especially of oil, by means of lipid vesicles without the need to introduce into the dispersion another stabilizing agent and especially an emulsifier. The vesicles described in these documents are obtained from ionic or nonionic lipids. However, these dispersions have the disadvantage of giving a sticky texture which makes their use unpleasant. This disadvantage is overcome by the choice of the oils.

Moreover, to obtain a sufficiently thick structure, gelling agents are generally added to these oil dispersions. Unfortunately, the nature of these vesicles limits the quantity of gelling agent to be used and therefore limits the consistency of the composition.

In addition, a cosmetic composition most often contains one or more active agents. However, this type of vesicle also limits the concentration of certain active agents. For example, glycerine can only be used in a limited quantity so that the texture is not sticky.

The need therefore still exists for dispersions which make it possible to overcome these disadvantages and which are pleasant to use whatever the compounds which they contain.

The applicant has found, unexpectedly, vesicles which make it possible to achieve these objectives.

SUMMARY OF THE INVENTION

Indeed, the applicant has found that a dispersion of vesicles which give a nonsticky texture could be obtained without being limited in the choice and/or the concentratic of the oils, the active agents or the gelling agents of the dispersion by using vesicles formed of a silicone surfactant.

Accordingly, the subject of the present invention is a dispersion in an external aqueous phase, of at least one water-immiscible liquid phase using lipid vesicles encapsulating an internal phase, characterized in that the lipid vesicles comprise a lamellar phase formed of at least one silicone surfactant.

The internal phase is generally an aqueous phase.

DETAILED DESCRIPTION OF THE INVENTION

A silicone surfactant is a silicone compound having at least a oxyethylenated and/or oxypropylenated chain. Silicone surfactants which may be used according to the present invention are those described in documents U.S. Pat. No. 5,364,633 and U.S. Pat. No. 5,411,744. These documents describe the use of silicone surfactants to prepare lipid vesicles. However, they do not describe or suggest that these vesicles can bring about the dispersion, in an aqueous phase, of a water-immiscible liquid. Now, it was not obvious, given the specific chemical nature of these surfactants, that the lamellar phase containing them can bring about a good dispersion of a water-immiscible phase in an aqueous phase without the addition of another stabilizing agent and especially of an emulsifier.

Moreover, it is known from documents EP-A-444983 and EP-A-526289 to prepare lipid vesicles containing an ionic or nonionic lipid combined with a silicone compound in the lamellar phase and to incorporate these vesicles in an aqueous dispersion which may contain oil. But the silicone compound described in these documents is not a constituent element of the vesicles; it constitutes only an additive which becomes intercalated between the sheets formed by the lipid, but is not a constituent element of these sheets. Indeed, they include an oil, gum or a silicone resin, the chemical constitution of which does not allow them to form vesicles. On the other hand, in the present invention, the silicone surfactant is the essential constituent component of the vesicles.

Advantageously, the silicone surfactant used according to the present invention is a compound of formula (I):

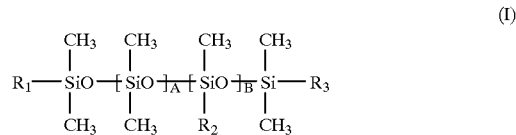

in which $R_1$, $R_2$, $R_3$, independently of each other, represent a $C_1$–$C_6$ alkyl radical or a radical —$(CH_2)_x$—$(OCH_2CH_2)_y$—$(OCH_2CH_2CH_2)_z$—$OR_4$, at least one radical $R_1$, $R_2$ or $R_3$ not being an alkyl radical; $R_4$ being hydrogen, an alkyl radical or an acyl radical;

A is an integer ranging from 0 to 200;

B is an integer ranging from 0 to 50; provided that A and B are not equal to zero at the same time;

x is an integer ranging from 1 to 6;

y is an integer ranging from 1 to 30;

z is an integer ranging from 0 to 5.

According to a preferred embodiment of the invention, in the compound of formula (I), the alkyl radical is a methyl radical, x is an integer ranging from 2 to 6 and y is an integer ranging from 4 to 30.

An example of silicone surfactants of formula (I) are the compounds of formula (II):

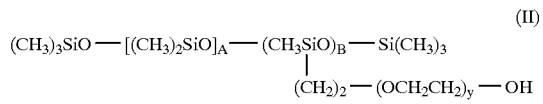

in which A is an integer ranging from 20 to 105, B is an integer ranging from 2 to 10 and y is an integer ranging from 10 to 20.

Another example of silicone surfactants of formula (I) are the compounds of formula (III):

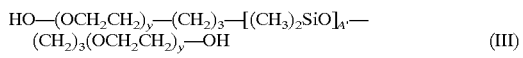

in which A' and y are integers ranging from 10 to 20.

As compounds of the invention, there may be used those sold by the company Dow Corning under the names DC 5329, DC 7439-146, DC 2-5696 and Q4 3667. The compounds DC 5329, DC 7439-146, DC 2-5695 are compounds of formula (II) where A is 22, B is 2 and y is 12; A is 103, B is 10 and y is 12; A is 27, B is 3 and y is 12, respectively.

The compound Q4-3667 is a compound of formula (III) where A' is 15 and y is 13.

The silicone surfactant is present in the dispersion in a quantity ranging from 0.1 to 40%, preferably from 1 to 10% by weight relative to the total weight of the dispersion.

The dispersions obtained with the vesicles according to the invention are not sticky on application to the skin and/or the hair contrary to the state of the art dispersions. In addition, they have a very soft, fluid and light texture and are, as a result, particularly advantageous as compositions for the treatment of greasy skins.

Advantageously, an ionic amphiphilic lipid may, in addition, be added to the silicone surfactant forming the vesicles. The addition of such a lipid enhances the stability of the dispersion according to the invention by inhibiting flocculation.

The ionic amphiphilic lipids used according to the invention may be chosen especially from the group formed by the neutralized anionic lipids, the amphoteric ionic lipids, the alkylsulphonic derivatives and mixtures thereof.

They are more particularly chosen from the group formed by:

the alkali metal salts of dicetyl- and dimyristylphosphate;

the alkali metal salts of cholesterol sulphate;

the alkali metal salts of cholesterol phosphate;

the lipoamino acids such as mono- and disodium acylglutamates;

the sodium salts of phosphatidic acid;

the phospholipids;

the alkylsulphonic derivatives of formula:

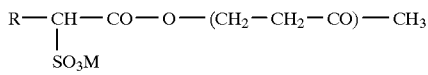

in which R represents $C_{16}$–$C_{22}$ alkyl, preferably $C_{16}H_{33}$ or $C_{18}C_{37}$, or a mixture thereof, and M is an alkali metal such as sodium and potassium;

and mixtures thereof.

Preferred ionic amphiphilic lipids include the monosodium salt of N-stearoylglutamic acid sold under the name "acylglutamate HS 21" by the company Ajinomoto, sodium dicetylphosphate and sodium dimyristylphosphate.

The amphiphilic ionic lipids are in particular present at concentrations ranging from 0 to 20% by weight, more particularly from 5 to 10% by weight relative to the weight of the silicone surfactant.

There may also be added to the silicone surfactant forming the vesicles at least one additive which makes it possible to reduce the permeability of the vesicles, to prevent their fusion and to increase the encapsulation level. The additive may be especially chosen from the group formed by sterols and especially phytosterols and cholesterol, long-chain alcohols and diols, long-chain amines and their quaternary ammonium derivatives, and mixtures thereof.

This additive may have a cosmetic and/or dermatological activity; this is the case, for example, for cholesterol.

The additives are in particular present in concentrations ranging from 0 to 50% by weight, more particularly from 5 to 40% by weight relative to the weight of the silicone surfactant.

According to the invention, water-immiscible liquid is understood to mean any liquid fatty substance, especially oil, fatty alcohol and fatty acid. Preferably, the water-immiscible liquid is an oil or a mixture of oils which may also contain other fatty substances such as fatty alcohols, fatty acids, waxes, gums.

Oils which may be used in the invention include mineral oils, vegetable oils such as jojoba oil, animal oils, synthetic oils, natural or synthetic essential oils, silicone oils such as silicone oil, fluorinated oils such as perfluoropolyethers, and halogenated hydrocarbons.

The vesicles according to the invention may contain, in a known manner, one or more active compounds, especially cosmetic and/or dermatological active agents which, depending on their solubility characteristics, may have various locations. If the active agents are water-soluble, they are present in the aqueous phase encapsulated in the vesicles. If the active agents are fat-soluble, they are present in the lipid phase constituting the lamellar phase. If the active agents are amphiphilic, they are distributed between the lipid phase and the encapsulated aqueous phase with a partition coefficient which varies according to the nature of the amphiphilic active agent and the respective compositions of the lipid phase and of the encapsulated aqueous phase.

The active agents may also be present in the external aqueous phase and/or in the water-immiscible liquid.

These active agents may be, inter alia, emollients, humectants, anti-free radical agents, antioxidants, anti-inflammatory agents, vitamins, depigmenting agents, anti-acne agents, anti-seborrhoeic agents, keratolytic agents, slimming agents, skin-colouring agents, sunscreens, essential oils, pigments, tanning-promoting agents, perfumes, colourings, melanin-regulating agents, anti-wrinkle and anti-aging agents, fat-regulating agents, antibacterial agents, antifungal agents, antiperspirants, deodorants, immunomodulatory agents, cicatrizing agents, vascular protecting agents, skin conditioning agents.

These active agents are used in the quantities customary in the relevant sectors.

Active agents contained in the vesicles according to the invention include, for example, polyols such as glycerine.

The aqueous phase of the dispersion may contain cosmetically and/or dermatologically acceptable adjuvants. These adjuvants include preservatives, gelling agents such as carbomer, and thickeners, colouring matter, perfumes, opacifiers.

The dispersion according to the invention may constitute especially a topical, in particular a cosmetic and/or dermatological, composition. For a topical application, the dispersion according to the invention contains a topically acceptable medium, that is to say compatible with the skin, the mucous membranes, the nails, the scalp and the hair.

The subject of the invention is also the use of the dispersion defined above for the cosmetic treatment of the skin and/or the mucous membranes and/or the nails and/or the scalp and/or the hair as well as for the preparation of a composition intended for the dermatological treatment of diseases of the skin and/or the mucous membranes and/or the nails and/or the scalp and/or the hair.

The subject of the invention is also a process for the nontherapeutic and/or therapeutic treatment of the skin and/or the mucous membranes and/or the nails and/or the scalp and/or the hair consisting in applying the above-defined dispersion to the skin and/or the mucous membranes and/or the nails and/or the scalp and/or the hair.

The dispersion according to the invention allows in particular the treatment of greasy skin. Accordingly, the present invention also relates to the use of the above-defined dispersion for the treatment of greasy skin.

The dispersion according to the invention may be provided in any of the clinical forms normally used for a topical application and may constitute especially a cream, a milk or a serum.

The example below of a composition according to the invention is given by way of illustration and with no limitation being implied. The quantities are given therein in % by weight.

EXAMPLE

Day cream for greasy skins

| First phase: | |
|---|---|
| Silicone surfactant (DC 2-5695) | 5% |
| Acylglutamate HS 21 | 0.6% |
| Glycerine | |
| Demineralized water | 60.6% |
| Second phase: | |
| Volatile silicone oil | 10% |
| Jojoba oil | 10% |
| Carbomer (Carbopol 980 sold by the company Goodrich) | 0.42% |
| Preservatives | 0.3% |
| Triethanolamine | qs pH 6 |
| Demineralized water | qs 100 |

To prepare the cream, the following procedure was followed: the silicone surfactant was mixed with acylglutamate, then the first phase was prepared by gradually wetting this mixture with the mixture of water and glycerine and by homogenizing it with the aid of a conventional mixer (Moritz). A suspension of vesicles whose size is of the order of 200 nm was obtained. The oily phase was then dispersed in the suspension of vesicles and the mixture was passed twice through a high-pressure homogenizer at 500 bar. The previously prepared neutralized Carbopol gel was then added.

This cream is a white, of fine and nonsticky texture which is pleasant to use.

The disclosure of French priority application 95-15292, filed Dec. 21, 1995 is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A composition, comprising:
   at least one water-immiscible liquid phase dispersed in an external aqueous phase containing lipid vesicles,
   wherein the vesicles comprise a lamellar phase formed of at least one silicone surfactant and encapsulate an internal phase.

2. The composition according to claim 1, wherein the internal phase is an aqueous phase.

3. The composition according to claim 1, wherein the silicone surfactant is a compound of formula (I):

$$R_1-\underset{\underset{CH_3}{|}}{\overset{\overset{CH_3}{|}}{Si}}O\underbrace{-\underset{\underset{CH_3}{|}}{\overset{\overset{CH_3}{|}}{Si}}O-}_{A}\underbrace{-\underset{\underset{R_2}{|}}{\overset{\overset{CH_3}{|}}{Si}}O-}_{B}\underset{\underset{CH_3}{|}}{\overset{\overset{CH_3}{|}}{Si}}-R_3 \quad (I)$$

in which $R_1$, $R_2$, $R_3$, independently of each other, represent a $C_1$–$C_6$ alkyl radical or a radical $-(CH_2)_x-(OCH_2CH_2)_y-(OCH_2CH_2CH_2)_z-OR_4$, at least one radical $R_1$, $R_2$ or $R_3$ not being an alkyl radical; $R_4$ being hydrogen, an alkyl radical or an acyl radical;

A is an integer ranging from 0 to 200;

B is an integer ranging from 0 to 50; provided that A and B are not equal to zero at the same time;

x is an integer ranging from 1 to 6;

y is an integer ranging from 1 to 30;

z is an integer ranging from 0 to 5.

4. The composition according to claim 3, wherein the silicone surfactant is a compound of formula (I) where the alkyl radical is a methyl radical, x is an integer ranging from 2 to 6 and is an integer ranging from 4 to 30.

5. The composition according to claim 3, wherein the silicone surfactant is a compound of formula (II):

$$(CH_3)_3SiO-[(CH_3)_2SiO]_A-(CH_3SiO)_B-Si(CH_3)_3 \atop \qquad\qquad\qquad\qquad\qquad | \atop \qquad\qquad\qquad\qquad\qquad (CH_2)_2-(OCH_2CH_2)_y-OH \quad (II)$$

in which A is an integer ranging from 20 to 105, B is an integer ranging from 2 to 10 and y is an integer ranging from 10 to 20.

6. The composition according to claim 5, wherein the silicone surfactant is selected from the compounds of formula (II) where A is 22, B is 2 and y is 12; A is 103, B is 10 and y is 12; A is 27, B is 3 and y is 12.

7. The composition according to claim 3, wherein the silicone surfactant is a compound of formula (III):

$$HO-(OCH_2CH_2)_y-(CH_2)_3-[(CH_3)_2SiO]_{A'}-(CH_2)_3(OCH_2CH_2)_y-OH \quad (III)$$

in which A' and y are integers ranging from 10 to 20.

8. The composition according to claim 7, wherein A' is 15 and y is 13.

9. The composition according to claim 1, wherein the silicone surfactant is present in a quantity ranging from 0.1 to 40% by weight relative to the total weight of the dispersion.

10. The composition according to claim 1, wherein the silicone surfactant is present in a quantity ranging from 1 to 10% by weight relative to the total weight of the dispersion.

11. The composition according to claim 1, wherein lamellar phase comprises, in addition, at least one ionic amphiphilic lipid.

12. The composition according to claim 11, wherein the ionic amphiphilic lipid is selected from the group consisting of neutralized anionic lipids, amphoteric ionic lipids, alkyl-sulphonic derivatives and mixtures thereof.

13. The composition according to claim 11, wherein the ionic amphiphilic lipid is selected from the group consisting of:

the alkali metal salts of dicetyl- and dimyristylphosphate;
the alkali metal salts of cholesterol sulphate;
the alkali metal salts of cholesterol phosphate;
the lipoamino acid salts;
the sodium salts of phosphatidic acid;
the phospholipids;
the alkylsulphonic derivatives of formula:

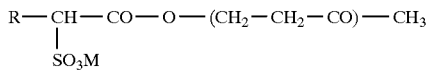

and mixtures thereof in which R represents $C_{16}$–$C_{22}$ alkyl, and M is an alkali metal;
and mixtures thereof.

14. The composition according to claim 11, wherein the ionic amphiphilic lipid is present in a concentration ranging from 5 to 10% by weight relative to the weight of the silicone surfactant.

15. The composition according to claim 1, wherein the lamellar phase comprises, in addition, at least one additive selected from the group consisting of sterols, long-chain alcohols and diols, long-chain amines and their quaternary ammonium derivatives, and mixtures thereof.

16. The composition according to claim 15, wherein the additive is cholesterol or a phytosterol.

17. The composition according to claim 15, wherein the additive is present in a concentration ranging from 5 to 40% by weight relative to the weight of the silicone surfactant.

18. The composition according to claim 1, wherein the internal phase of the vesicles contains at least one cosmetic or dermatological active agent.

19. The composition according to claim 1, wherein the water-immiscible liquid is an oil.

20. The composition of claim 1, which is a cosmetic and/or dermatological composition.

21. A process for treatment of a substrate selected from the group consisting of the skin, mucous membranes, nails, scalp, and hair and mixtures thereof, comprising applying the composition according to claim 1 to said substrate.

22. The process of claim 21, wherein the treatment is cosmetic.

23. The process of claim 21, wherein the treatment is dermatological.

24. The process of claim 21, wherein the treatment is of greasy skin.

25. The process of claim 21, wherein the treatment is nontherapeutic.

26. A method of making the composition of claim 1, comprising:

combining an aqueous phase containing lipid vesicles with a one water-immiscible liquid phase to produce said composition.

* * * * *